United States Patent
Mozes et al.

(10) Patent No.: US 12,251,169 B2
(45) Date of Patent: Mar. 18, 2025

(54) METHOD OF REGISTERING AN IMAGING SCAN WITH A COORDINATE SYSTEM AND ASSOCIATED SYSTEMS

(71) Applicant: Neocis Inc., Miami, FL (US)

(72) Inventors: Alon Mozes, Miami Beach, FL (US); Alexandra Bellettre, Salt Lake City, UT (US)

(73) Assignee: NEOCIS INC., Miami, FL (US)

( * ) Notice: Subject to any disclaimer, the term of this patent is extended or adjusted under 35 U.S.C. 154(b) by 626 days.

(21) Appl. No.: 17/430,993

(22) PCT Filed: Feb. 14, 2020

(86) PCT No.: PCT/IB2020/051263
§ 371 (c)(1),
(2) Date: Aug. 13, 2021

(87) PCT Pub. No.: WO2020/165856
PCT Pub. Date: Aug. 20, 2020

(65) Prior Publication Data
US 2022/0160431 A1 May 26, 2022

Related U.S. Application Data

(60) Provisional application No. 62/806,025, filed on Feb. 15, 2019.

(51) Int. Cl.
*A61B 34/20* (2016.01)
*A61B 6/03* (2006.01)
(Continued)

(52) U.S. Cl.
CPC .............. *A61B 34/20* (2016.02); *A61B 6/032* (2013.01); *A61B 6/512* (2024.01); *A61B 34/10* (2016.02);
(Continued)

(58) Field of Classification Search
CPC . A61B 34/20; A61B 2034/2055; A61B 5/055; A61B 2034/107; A61B 2034/2051;
(Continued)

(56) References Cited

U.S. PATENT DOCUMENTS 6,402,707 B1 6/2002 Ernst
9,554,869 B1 * 1/2017 Huang .................. A61B 5/055
(Continued)

FOREIGN PATENT DOCUMENTS

CN 102551892 A 7/2012
CN 106572831 A 4/2017
(Continued)

OTHER PUBLICATIONS

BrainLab: "Surface Matching with Z-touch and Softouch," Sep. 30, 2015, p. 1, XP054980382, Retrieved from the Internet: https://www.youtube.com/watch?y=C9ngfY9?Bkg [retrieved on Apr. 16, 2020].

*Primary Examiner* — Ajibola A Akinyemi
(74) *Attorney, Agent, or Firm* — Womble Bond Dickinson (US) LLP

(57) ABSTRACT

A method of relating an object to a coordinate system, the object being supported by a support element, and the object and the support element being housed within a housing, includes engaging a registration element with the object or the support element, conducting an optical surface scan of the object and the registration element, using an optical
(Continued)

scanner, to form a three-dimensional surface image of the object, the three-dimensional surface image having the coordinate system associated therewith, with the registration element being associated with the coordinate system, and correlating the object with the registration element in the three-dimensional surface image so as to register the object with the coordinate system. Associated methods and systems are also provided.

21 Claims, 6 Drawing Sheets

(51) Int. Cl.
  *A61B 6/51* (2024.01)
  *A61B 34/10* (2016.01)
  *A61B 34/30* (2016.01)
  *A61B 90/00* (2016.01)

(52) U.S. Cl.
  CPC .............. *A61B 34/30* (2016.02); *A61B 90/37* (2016.02); *A61B 2034/105* (2016.02); *A61B 2034/2057* (2016.02); *A61B 2034/2065* (2016.02); *A61B 2034/2068* (2016.02); *A61B 2090/364* (2016.02); *A61B 2090/373* (2016.02); *A61B 2090/3762* (2016.02)

(58) Field of Classification Search
  CPC . A61B 34/10; A61B 90/36; A61B 2034/2057; A61B 2034/2065; A61B 2090/363; A61B 5/062; A61B 2090/3945; A61B 2090/3983; A61B 5/06; A61B 90/39
  USPC ........................................................ 382/128
  See application file for complete search history.

(56) References Cited

U.S. PATENT DOCUMENTS

| | | | |
|---|---|---|---|
| 2010/0124367 | A1 | 5/2010 | Cizek |
| 2011/0045428 | A1 | 2/2011 | Boltunov et al. |
| 2013/0172731 | A1* | 7/2013 | Gole ..................... A61B 6/506 |
| | | | 600/424 |
| 2013/0249907 | A1 | 9/2013 | Humphries et al. |
| 2013/0301800 | A1* | 11/2013 | Gertner ................ A61N 5/1045 |
| | | | 378/65 |
| 2013/0322719 | A1 | 12/2013 | Dekel et al. |
| 2015/0057675 | A1 | 2/2015 | Akeel et al. |
| 2017/0135655 | A1 | 5/2017 | Wang et al. |
| 2018/0028292 | A1 | 2/2018 | Pesach et al. |
| 2018/0078332 | A1 | 3/2018 | Mozes et al. |
| 2018/0263707 | A1 | 9/2018 | Sela et al. |
| 2018/0296283 | A1 | 10/2018 | Crawford et al. |
| 2019/0290365 | A1 | 9/2019 | Gao |

FOREIGN PATENT DOCUMENTS

| | | |
|---|---|---|
| JP | 2000-333971 | 12/2000 |
| KR | 10-1678910 | 12/2016 |
| KR | 10-1678910 B1 | 12/2016 |
| KR | 10-1913586 B1 | 11/2018 |

* cited by examiner

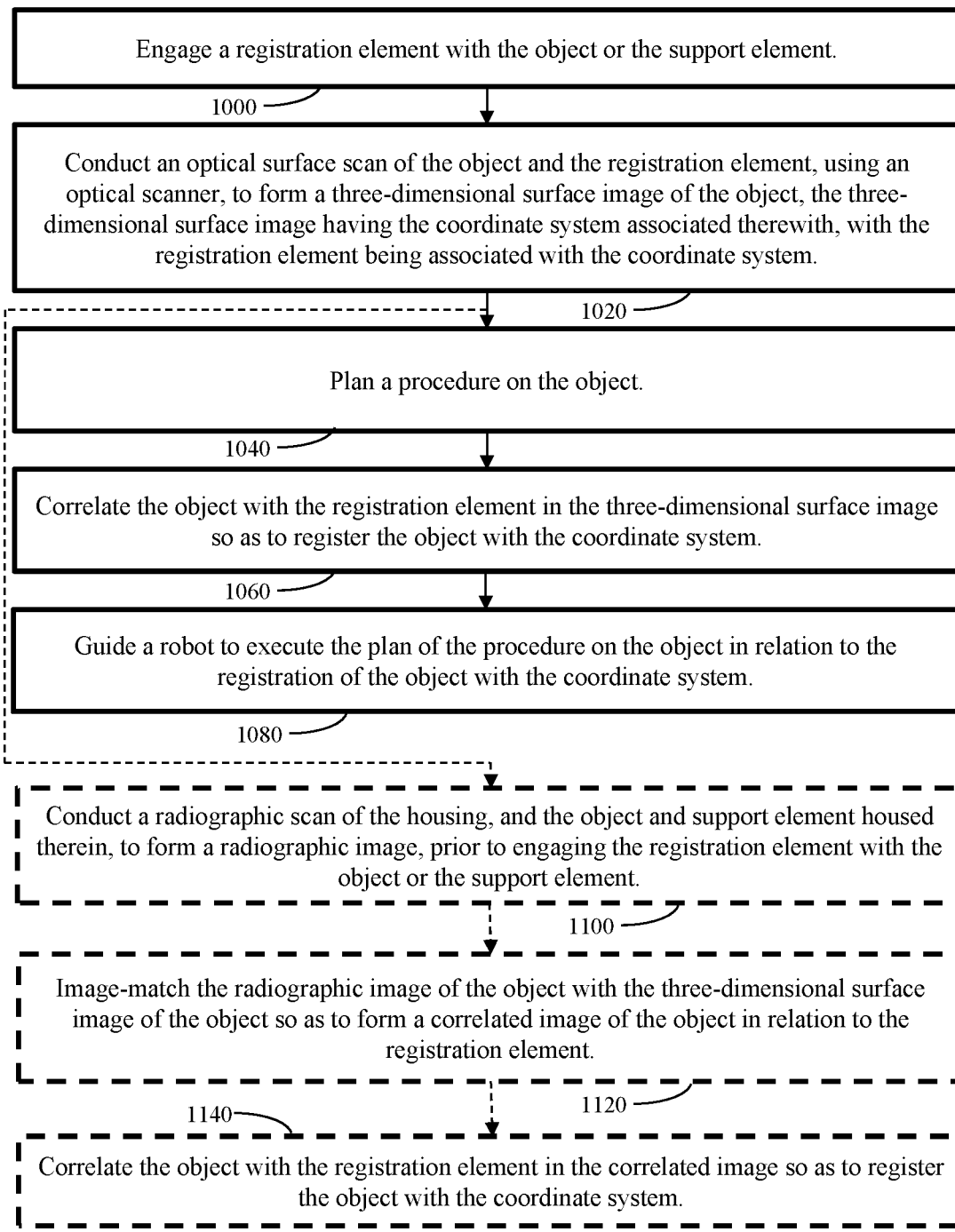

METHOD OF REGISTERING AN IMAGING SCAN WITH A COORDINATE SYSTEM AND ASSOCIATED SYSTEMS

CROSS-REFERENCE TO RELATED APPLICATIONS

This application is a national stage filing under 35 U.S.C. 371 of PCT/IB2020/051263, filed Feb. 14, 2020, which International Application was published by the International Bureau in English on Aug. 20, 2020, as WO 2020/165856, and application claims priority from U.S. Provisional Application No. 62/806,025, filed Feb. 15, 2019, which applications are hereby incorporated in their entirety by reference in this application.

BACKGROUND

Field of the Disclosure

The present disclosure relates to imaging procedures and, more particularly, to methods and systems for registering an imaging scan with a coordinate system so as to allow the imaging scan to be implemented in guidance of a robot such as a surgical robot.

Description of Related Art

Preoperative imaging, particularly in the surgical space, and more particularly in the dental surgical space, may involve several different processes. For example, one preoperative imaging process involves planning in advance, but also requires that the patient to undergo two CT imaging scans. The first CT imaging scan is generally taken weeks in advance of the scheduled surgery, and the resulting imaging of the patient is used for the planning for the procedure (i.e., the plan for the surgical procedure is planned in relation to and using the first CT imaging scan). The second CT imaging scan is then taken on the day of the surgical procedure with a fiducial marker (or array or fiducial beads) in place on the patient during the second CT imaging scan. The image from the second CT imaging scan (including the fiducial marker/array in the image) is then matched/registered with the image from the first CT imaging scan, for example, based on an alignment of imaged features (e.g., anatomical features) between the images from both imaging scans. The advance plan for the surgical procedure associated with the image from the first CT imaging scan is then imported into association with the image from the second CT imaging scan. The image from the second CT imaging scan also includes the fiducial marker (or array) therein. As such, once the imaged features (e.g., anatomical features) are theoretically aligned between the two images such that the two CT imaging scans are in registration, the advance plan for the surgical procedure on the patient and/or the locations of the imaged features (e.g., anatomical features) of the patient will also be in registration with the fiducial marker (or array) attached to the patient and will thus be translated to a Patient Coordinate Space.

Such a procedure, however, may be subject to inaccuracies. For example, if the patient's anatomy changes or shifts between the first and second CT imaging scans, it may be difficult to align the imaged features between the images and/or the fiducial marker may end up registered in relation to an anatomical approximation in the actual Patient Coordinate Space. Thus, there exists a need for a simplified procedure for creating an imaged-based plan for a surgical procedure that minimizes the number of required CT scans. Moreover, there exists a need for such a procedure that minimizes the risk of change to the patient's anatomy between the planning stage and the surgical procedure stage. In addition, there exists a need for such a procedure that reliably and consistently registers the image(s) of the patient's anatomy (imaged features) and the fiducial marker in the actual Patient Coordinate Space such that the surgical plan can be executed with greater precision.

SUMMARY OF THE DISCLOSURE

The above and other needs are met by aspects of the present disclosure which, in one aspect, provides a method of relating an object to a coordinate system, with the object being supported by a support element, and with the object and the support element being housed within a housing. Such a method comprises engaging a registration element with the object or the support element; conducting an optical surface scan of the object and the registration element, using an optical scanner, to form a three-dimensional surface image of the object, the three-dimensional surface image having the coordinate system associated therewith, with the registration element being associated with the coordinate system; and correlating the object with the registration element in the three-dimensional surface image so as to register the object with the coordinate system.

Another aspect provides a method of controlling a robot with respect to an object in a coordinate system, with the object being supported by a support element, and the object and the support element being housed within a housing. Such a method comprises engaging a registration element with the object or the support element; conducting an optical surface scan of the object and the registration element, using an optical scanner, to form a three-dimensional surface image of the object, the three-dimensional surface image having the coordinate system associated therewith, with the registration element being associated with the coordinate system; planning a procedure on the object; correlating the object with the registration element in the three-dimensional surface image so as to register the object with the coordinate system; and guiding a robot to execute the plan of the procedure on the object in relation to the registration of the object with the coordinate system.

In some aspects, a radiographic scan of the housing, and the object and support element housed therein, is conducted to form a radiographic image, prior to engaging the registration element with the object or the support element. The radiographic image of the object is then image-matched with the three-dimensional surface image of the object so as to form a correlated image of the object in relation to the registration element. The object is then correlated with the registration element in the correlated image so as to register the object with the coordinate system.

Another aspect provides a system for relating an object to a coordinate system, with the object being supported by a support element, and with the object and the support element being housed within a housing. Such a system comprises a registration element adapted to be engaged with the object or the support element; an optical scanner arranged to conduct an optical surface scan of the object and the registration element and to form a three-dimensional surface image of the object, wherein the registration element is associated with the coordinate system and the three-dimensional surface image has the coordinate system associated therewith; and a controller having a processor and being in communication with the optical scanner, wherein the controller is arranged to correlate the object with the registration element in the three-dimensional surface image so as to register the object with the coordinate system.

Yet another aspect provides a system for guiding a robot in relation to an object in a coordinate system, with the object being supported by a support element, and with the object and the support element being housed within a housing. Such a method comprises a registration element adapted to be engaged with the object or the support element; an optical scanner arranged to conduct an optical surface scan of the object and the registration element and to form a three-dimensional surface image of the object, wherein the registration element is associated with the coordinate system and the three-dimensional surface image has the coordinate system associated therewith; and a controller having a processor and being in communication with the optical scanner, wherein the controller is arranged to allow formation of a plan of a procedure on the object, to correlate the object with the registration element in the three-dimensional surface image so as to register the object with the coordinate system, and to guide a robot to execute the plan of the procedure on the object in relation to the registration of the object with the coordinate system.

In some aspects, a computerized tomography device is arranged to conduct a radiographic scan of the housing, and the object and support element housed therein, to form a radiographic image, prior to the registration element being engaged with the object or the support element, wherein the controller is arranged to be in communication with the computerized tomography device, to image-match the radiographic image of the object with the three-dimensional surface image of the object so as to form a correlated image of the object in relation to the registration element, and to correlate the object with the registration element in the correlated image so as to register the object with the coordinate system.

The present disclosure thus includes, without limitation, the following embodiments:

Example implementation 1: A method of relating an object to a coordinate system, the object being supported by a support element, the object and the support element being housed within a housing, the method comprising engaging a registration element with the object or the support element; conducting an optical surface scan of the object and the registration element, using an optical scanner, to form a three-dimensional surface image of the object, the three-dimensional surface image having the coordinate system associated therewith, with the registration element being associated with the coordinate system; and correlating the object with the registration element in the three-dimensional surface image so as to register the object with the coordinate system.

Example implementation 2: The method of any preceding embodiment, or any combination of preceding embodiments, comprising conducting a radiographic scan of the housing, and the object and support element housed therein, to form a radiographic image, prior to engaging the registration element with the object or the support element; image-matching the radiographic image of the object with the three-dimensional surface image of the object so as to form a correlated image of the object in relation to the registration element; and correlating the object with the registration element in the correlated image so as to register the object with the coordinate system.

Example implementation 3: The method of any preceding embodiment, or any combination of preceding embodiments, wherein image-matching the radiographic image with the three-dimensional surface image comprises image-matching a three-dimensional structural representation of the object and the support element provided by the radiographic scan with the three-dimensional surface image of the object, the support element, and the registration element provided by the optical surface scan.

Example implementation 4: The method of any preceding embodiment, or any combination of preceding embodiments, wherein the registration element is not radiopaque.

Example implementation 5: The method of any preceding embodiment, or any combination of preceding embodiments, wherein the optical scanner is operably engaged with a distal end of a robot tracking arm registered with the coordinate system.

Example implementation 6: The method of any preceding embodiment, or any combination of preceding embodiments, wherein the registration element is arranged to be in a known relation with the coordinate system.

Example implementation 7: The method of any preceding embodiment, or any combination of preceding embodiments, wherein engaging the registration element with the object or the support element comprises engaging the registration element with a reference frame; and engaging the reference frame with the object or the support element.

Example implementation 8: The method of any preceding embodiment, or any combination of preceding embodiments, comprising planning a procedure on the object in relation to the three-dimensional surface image thereof prior to correlating the object with the registration element in the three-dimensional surface image thereof.

Example implementation 9: A method of controlling a robot with respect to an object in a coordinate system, the object being supported by a support element, the object and the support element being housed within a housing, the method comprising engaging a registration element with the object or the support element; conducting an optical surface scan of the object and the registration element, using an optical scanner, to form a three-dimensional surface image of the object, the three-dimensional surface image having the coordinate system associated therewith, with the registration element being associated with the coordinate system; planning a procedure on the object; correlating the object with the registration element in the three-dimensional surface image so as to register the object with the coordinate system; and guiding a robot to execute the plan of the procedure on the object in relation to the registration of the object with the coordinate system.

Example implementation 10: The method of any preceding embodiment, or any combination of preceding embodiments, comprising conducting a radiographic scan of the housing, and the object and support element housed therein, to form a radiographic image, prior to engaging the registration element with the object or the support element; image-matching the radiographic image of the object with the three-dimensional surface image of the object so as to form a correlated image of the object in relation to the registration element; and correlating the object with the registration element in the correlated image so as to register the object with the coordinate system.

Example implementation 11: The method of any preceding embodiment, or any combination of preceding embodiments, wherein image-matching the radiographic image with the three-dimensional surface image comprises image-matching a three-dimensional structural representation of the object and the support element provided by the radiographic scan with the three-dimensional surface image of the object, the support element, and the registration element provided by the optical surface scan.

Example implementation 12: The method of any preceding embodiment, or any combination of preceding embodiments, wherein planning the procedure on the object comprises planning the procedure on the object in relation to the three-dimensional surface image thereof, the radiographic image thereof, or the correlated image thereof including the three-dimensional surface image and the radiographic image.

Example implementation 13: The method of any preceding embodiment, or any combination of preceding embodiments, wherein the registration element is not radiopaque.

Example implementation 14: The method of any preceding embodiment, or any combination of preceding embodiments, wherein the optical scanner is operably engaged with a distal end of a robot tracking arm registered with the coordinate system and arranged to be in communication with the robot.

Example implementation 15: The method of any preceding embodiment, or any combination of preceding embodiments, wherein the registration element is arranged to be in a known relation with the coordinate system.

Example implementation 16: The method of any preceding embodiment, or any combination of preceding embodiments, wherein engaging the registration element with the object or the support element comprises engaging the registration element with a reference frame; and engaging the reference frame with the object or the support element.

Example implementation 17: The method of any preceding embodiment, or any combination of preceding embodiments, wherein planning a procedure on the object comprises planning a procedure on the object prior to correlating the object with the registration element in the correlated image thereof.

Example implementation 18: A system for relating an object to a coordinate system, the object being supported by a support element, the object and the support element being housed within a housing, the system comprising a registration element adapted to be engaged with the object or the support element; an optical scanner arranged to conduct an optical surface scan of the object and the registration element and to form a three-dimensional surface image of the object, the registration element being associated with the coordinate system and the three-dimensional surface image having the coordinate system associated therewith; and a controller having a processor and being in communication with the optical scanner, the controller being arranged to correlate the object with the registration element in the three-dimensional surface image so as to register the object with the coordinate system.

Example implementation 19: The system of any preceding embodiment, or any combination of preceding embodiments, comprising a computerized tomography device arranged to conduct a radiographic scan of the housing, and the object and support element housed therein, to form a radiographic image, prior to the registration element being engaged with the object or the support element, wherein the controller is arranged to be in communication with the computerized tomography device, to image-match the radiographic image of the object with the three-dimensional surface image of the object so as to form a correlated image of the object in relation to the registration element, and to correlate the object with the registration element in the correlated image so as to register the object with the coordinate system.

Example implementation 20: The system of any preceding embodiment, or any combination of preceding embodiments, wherein the controller is arranged to image-match a three-dimensional structural representation of the object and the support element provided by the radiographic scan with the three-dimensional surface image of the object, the support element, and the registration element provided by the optical surface scan.

Example implementation 21: The system of any preceding embodiment, or any combination of preceding embodiments, wherein the registration element is not radiopaque.

Example implementation 22: The system of any preceding embodiment, or any combination of preceding embodiments, wherein the optical scanner is operably engaged with a distal end of a robot tracking arm registered with the coordinate system and arranged to be in communication with the controller.

Example implementation 23: The system of any preceding embodiment, or any combination of preceding embodiments, wherein the registration element is arranged to be in a known relation with the coordinate system.

Example implementation 24: The system of any preceding embodiment, or any combination of preceding embodiments, comprising a reference frame having the registration element engaged therewith, the reference frame being engaged with the object or the support element.

Example implementation 25: The system of any preceding embodiment, or any combination of preceding embodiments, wherein the controller is arranged to allow formation of a plan of a procedure on the object in relation to the three-dimensional surface image thereof prior to the object being correlated with the registration element in the three-dimensional surface image thereof.

Example implementation 26: The system of any preceding embodiment, or any combination of preceding embodiments, wherein the controller is arranged to track a position of the robot tracking arm and the optical scanner operably engaged with the distal end thereof in relation to the coordinate system.

Example implementation 27: A system for guiding a robot in relation to an object, the object being supported by a support element, the object and the support element being housed within a housing, the method comprising a registration element adapted to be engaged with the object or the support element; an optical scanner arranged to conduct an optical surface scan of the object and the registration element and to form a three-dimensional surface image of the object, the registration element being associated with the coordinate system and the three-dimensional surface image having the coordinate system associated therewith; and a controller having a processor and being in communication with the optical scanner, the controller being arranged to allow formation of a plan of a procedure on the object, to correlate the object with the registration element in the three-dimensional surface image so as to register the object with the coordinate system, and guide a robot to execute the plan of the procedure on the object in relation to the registration of the object with the coordinate system.

Example implementation 28: The system of any preceding embodiment, or any combination of preceding embodiments, comprising a computerized tomography device arranged to conduct a radiographic scan of the housing, and the object and support element housed therein, to form a radiographic image, prior to the registration element being engaged with the object or the support element, wherein the controller is arranged to be in communication with the computerized tomography device, to image-match the radiographic image of the object with the three-dimensional surface image of the object so as to form a correlated image of the object in relation to the registration element, and to correlate the object with the registration element in the correlated image so as to register the object with the coordinate system.

Example implementation 29: The system of any preceding embodiment, or any combination of preceding embodiments, wherein controller is arranged to image-match a three-dimensional structural representation of the object and the support element provided by the radiographic scan with the three-dimensional surface image of the object, the support element, and the registration element provided by the optical surface scan.

Example implementation 30: The system of any preceding embodiment, or any combination of preceding embodiments, wherein the controller is arranged to allow formation of the plan of the procedure on the object in relation to the three-dimensional surface image thereof, the radiographic image thereof, or the correlated image thereof including the three-dimensional surface image and the radiographic image.

Example implementation 31: The system of any preceding embodiment, or any combination of preceding embodiments, wherein the registration element is not radiopaque.

Example implementation 32: The system of any preceding embodiment, or any combination of preceding embodiments, wherein the optical scanner is operably engaged with a distal end of a robot tracking arm registered with the coordinate system and arranged to be in communication with the controller and the robot.

Example implementation 33: The system of any preceding embodiment, or any combination of preceding embodiments, wherein the registration element is arranged to be in a known relation with the coordinate system.

Example implementation 34: The system of any preceding embodiment, or any combination of preceding embodiments, comprising a reference frame having the registration element engaged therewith, the reference frame being engaged with the object or the support element.

Example implementation 35: The system of any preceding embodiment, or any combination of preceding embodiments, wherein the controller is arranged to allow formation of a plan of a procedure on the object in relation to the three-dimensional surface image thereof prior to the object being correlated with the registration element in the correlated image thereof.

Example implementation 36: The system of any preceding embodiment, or any combination of preceding embodiments, wherein the controller is arranged to track a position of the robot tracking arm and the optical scanner operably engaged with the distal end thereof in relation to the coordinate system.

These and other example implementations, features, aspects, and advantages of the present disclosure will be apparent from a reading of the following detailed description together with the accompanying drawings, which are briefly described below. The present disclosure includes any combination of two, three, four, or more features or elements set forth in this disclosure or recited in any one or more of the claims, regardless of whether such features or elements are expressly combined or otherwise recited in a specific embodiment description or claim herein. This disclosure is intended to be read holistically such that any separable features or elements of the disclosure, in any of its aspects and embodiments, should be viewed as intended to be combinable, unless the context of the disclosure clearly dictates otherwise.

Thus, the methods according to aspects of the present disclosure provide these and other advantages, as detailed further herein. Importantly, these advantages include reducing or eliminating the need for a second radiographic scan as part of a pre-operative process for a robotic surgical procedure. That is, by taking an optical three-dimensional surface scan of the feature of interest (e.g., an intra-oral scan) and including the fiducial marker array (e.g., mounted on the splint, with the splint engaged with the patient) in the intra-oral scan, the imaged fiducial marker array in the scan is used to register the optical three-dimensional surface scan with the patient and/or the locations of the features (e.g., anatomical features). Once the optical three-dimensional surface scan is registered with the coordinate system associated with the fiducial marker array engaged with the patient, the imaged features (e.g., the three-dimension surface image of the anatomy) from the intra-oral scan can be can be registered with the imaged features (e.g., the radiographic image of the structure of the anatomy) from the original/first CT scan. The plan for the procedure and other information associated therewith, developed from the original/first CT scan, can then be applied in reference to the patient and/or the locations of the anatomical features of the patient (e.g., within the coordinate system associated with the fiducial marker array).

In further aspects, the optical three-dimensional surface scan (e.g., intra-oral scan) may obviate the need for both the first and second CT scans. For example, in some cases, the surgeon may not need a CT (e.g., radiographic imaging of anatomical features) to accomplish the intended procedure. This could be applicable to robotic procedures beyond, for instance, dental implants, and extend to, for instance, a tooth preparation procedure involving drilling or abrading away a tooth surface (e.g., to eliminate decayed areas of the tooth) and prepare the remaining portion of the tooth for receiving a crown (e.g., a prosthetic tooth) thereon. In such instances, the intra-oral scan alone may be sufficient for the purpose of planning the procedure, and the fiducial marker array included in the intra-oral scan can be used to register the intra-oral scan with the patient and/or the locations of the features of the patient (e.g., within the coordinate system associated with the fiducial marker array), and to implement robot guidance.

BRIEF DESCRIPTION OF THE SEVERAL VIEWS OF THE DRAWINGS

Figure 1:
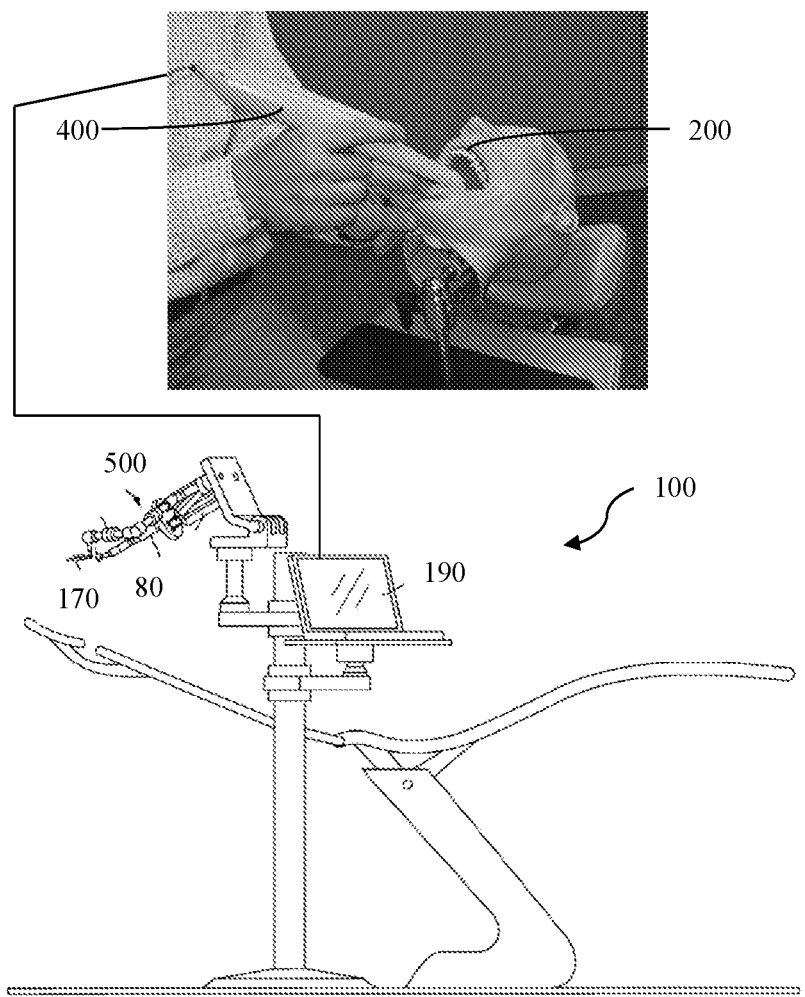
Figure 1A:
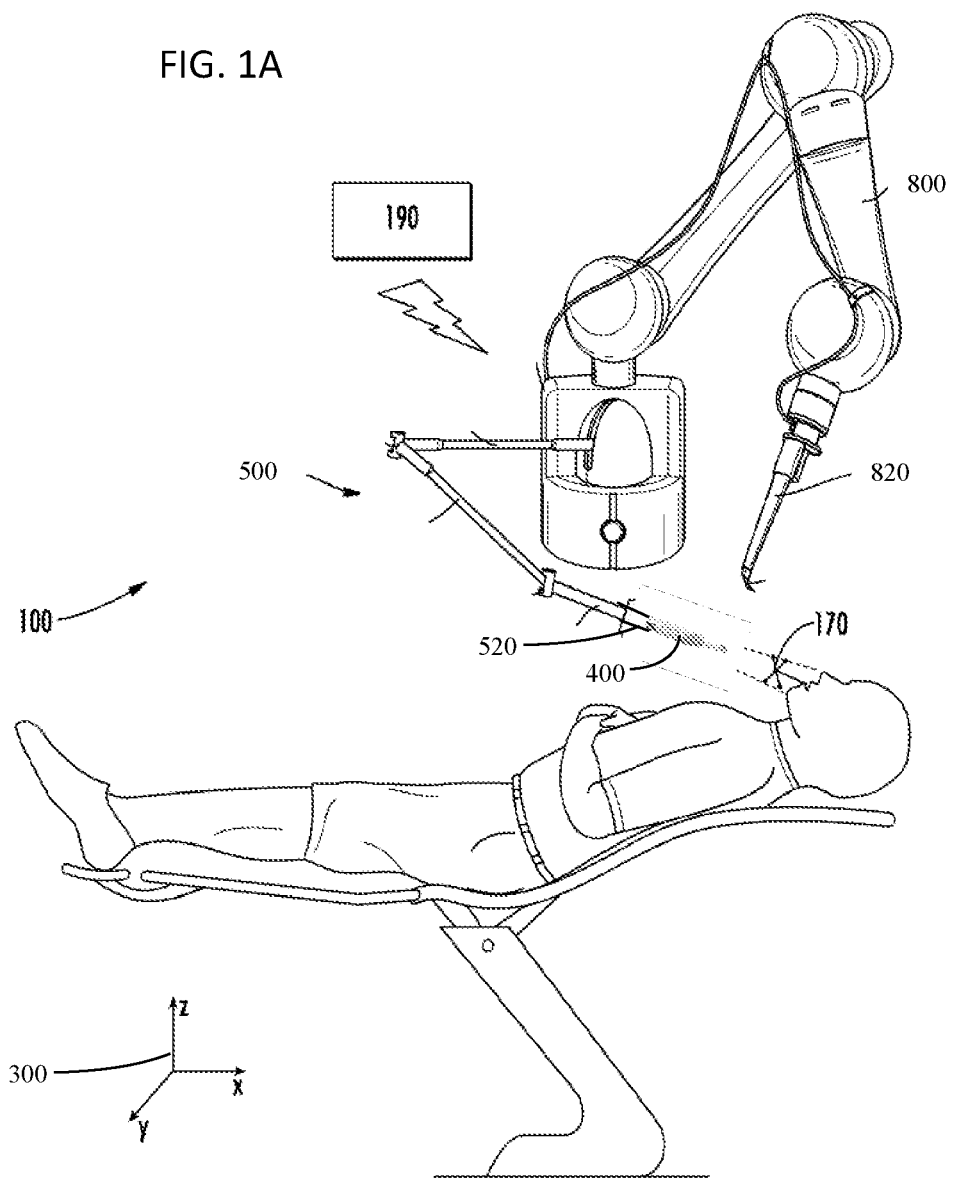
Figure 2:
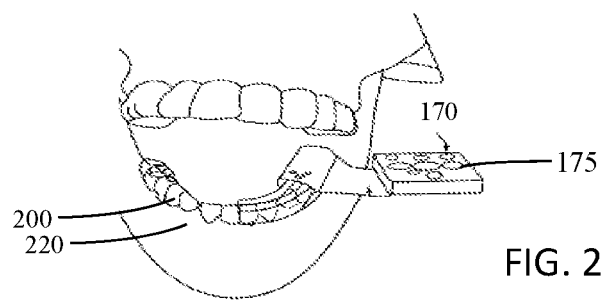
Figure 3:
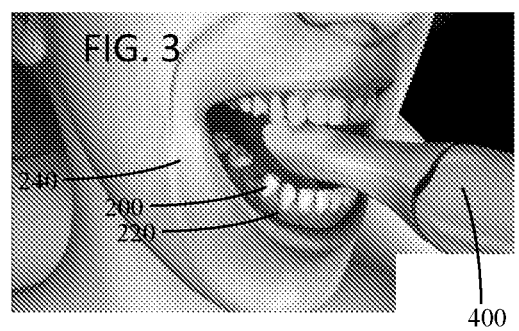
Figure 4:
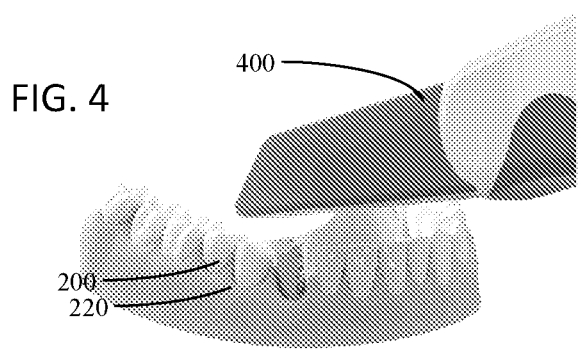
Figure 5:
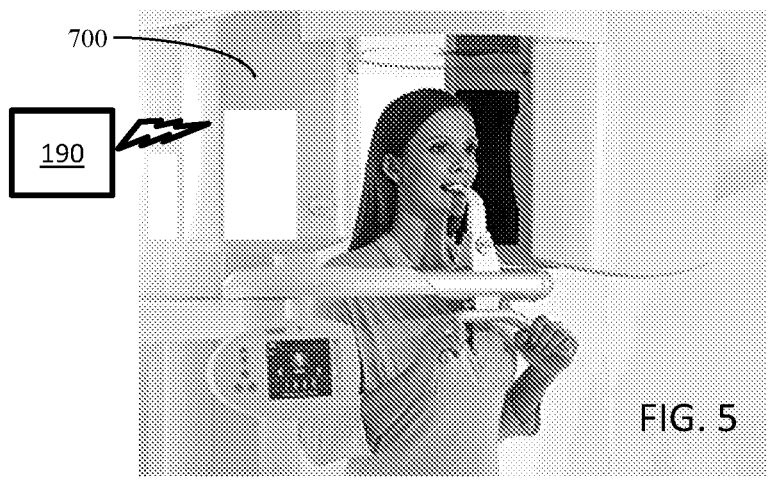
Figure 6:
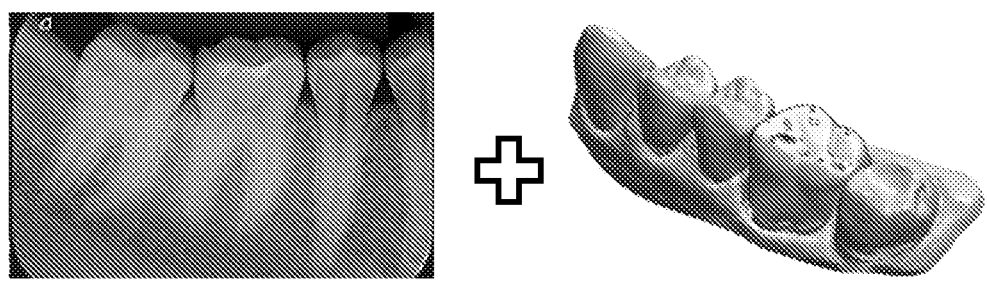
Figure 7:
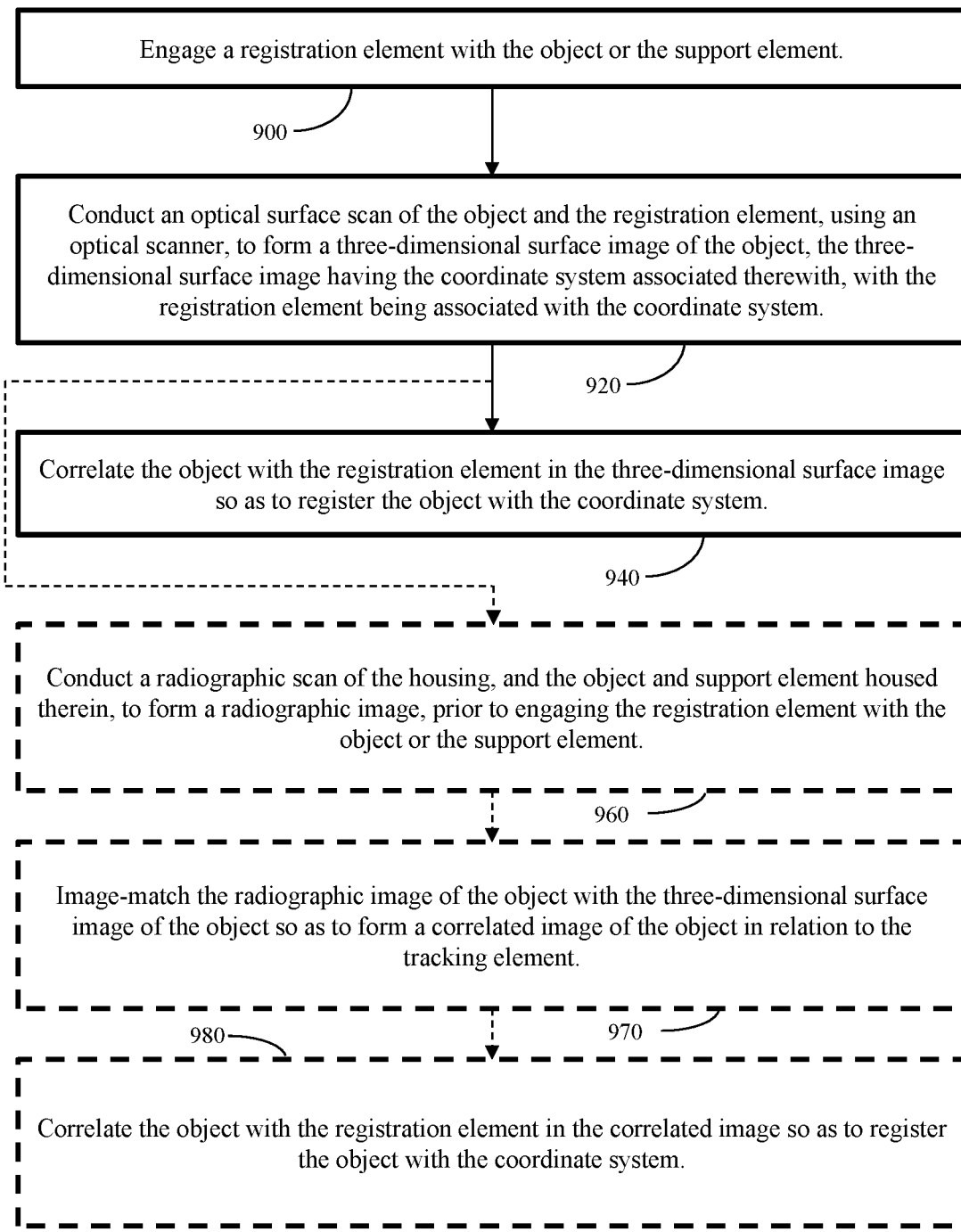

Having thus described the disclosure in general terms, reference will now be made to the accompanying drawings, which are not necessarily drawn to scale, and wherein:

FIG. 1 schematically illustrates an optical scanner arranged to conduct an optical surface scan of the object, wherein the object may be housed within a housing including the mouth or maxillofacial structure of a patient, in a system for relating an object to a coordinate system, as well as for controlling a robot with respect to an object in a coordinate system, according to one aspect of the present disclosure;

FIG. 1A schematically illustrates an optical scanner arranged to conduct an optical surface scan of the object, wherein the object may be housed within a housing including the mouth or maxillofacial structure of a patient, in a system for relating an object to a coordinate system, as well as for controlling a robot with respect to an object in a coordinate system, according to one aspect of the present disclosure;

FIG. 2 schematically illustrates an object supported by a support element, wherein the object includes a tooth and the support element include a corresponding jaw and/or gums, and wherein a registration element is adapted to be engaged with the object or the support element, according to one aspect of the present disclosure;

FIGS. 3 and 4 schematically illustrate an optical scanner arranged to conduct an optical surface scan of the object, wherein the object may be housed within a housing including the mouth or maxillofacial structure of a patient, according to one aspect of the present disclosure;

FIG. 5 schematically illustrates a computerized tomography device arranged to conduct a radiographic scan of the housing, and the object and support element housed therein, to form a radiographic image thereof, according to one aspect of the present disclosure;

FIG. 6 schematically illustrates a radiographic image of the object being image-matched with a three-dimensional surface image of the object, according to one aspect of the present disclosure;

FIG. 7 schematically illustrates a method of relating an object to a coordinate system, according to one aspect of the present disclosure; and FIG. 8 schematically illustrates a method of controlling a robot with respect to an object in a coordinate system, according to one aspect of the present disclosure.

DETAILED DESCRIPTION OF THE DISCLOSURE

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure is embodied in many different forms and should not be construed as limited to the embodiments set forth herein; rather, these embodiments are provided so that this disclosure will satisfy applicable legal requirements. The various aspects of the present disclosure previously mentioned, as well as many other aspects of the disclosure, are described in further detail herein.

Aspects of the present disclosure, as shown, for example, in FIG. 1-4, involve a system 100 for relating an object 200 to a coordinate system 300, as well as controlling a robot 800 with respect to an object 200 in a coordinate system 300, wherein the object 200 is supported by a support element 220, and wherein the object 200 and the support element 220 are housed within a housing 240. In one example, the object 200 may include a tooth, the support element 220 may include the corresponding jaw and/or gums, and the housing 240 may include the mouth or maxillofacial structure of a patient. In one particular aspect, such a system 100 comprises a registration element 170 adapted to be engaged with the object 200 or the support element 220 (see, e.g., FIG. 2). An optical scanner 400 is arranged to conduct an optical surface scan of the object 200 (see, e.g., FIGS. 3 and 4) and the registration element 170 and to form a three-dimensional surface image (see, e.g., FIG. 6, right side image) of the object 200. The optical scanner 400 is arranged to be hand held and manually manipulated by and operator (see, e.g., FIG. 1), or may otherwise be operably engaged with a distal end 520 of a robot tracking arm 500 (see, e.g., FIG. 1A). The three-dimensional surface image has the coordinate system 300 associated therewith, and the registration element 170 is associated with the coordinate system 300. The registration element 170 adapted to be engaged with the object 200 or the support element 220 (see, e.g., FIG. 2) may comprise, for example, one or more fiducial markers 175 arranged to define or be in a known relation to the coordinate system 300. More particularly, in some instances, the one or more fiducial markers 175 may be arranged such that at least the location and orientation of the one or more fiducial markers 175 is known or readily determinable in relation to or registration with the coordinate system 300. A controller 190 has a processor, and is arranged to be in communication with the optical scanner 400 and, in some instances, with the robot tracking arm 500. The controller 190 is further arranged to correlate the object 200 with the registration element 170 in the three-dimensional surface image so as to register the object 200 with the coordinate system 300. That is, since the registration element 170 has one or more fiducial markers 175 that themselves define a known position/orientation or reference or registration in the coordinate system 300, the optical surface scan of the object 200/support element 220 including the registration element 170 allows the object 200 to be spatially correlated with registration element 170 based on the three-dimensional surface image. When the spatial correlation of the object 200 is known in relation to the registration element 170 and with respect to the coordinate system 300, the object 200 thus becomes registered in the coordinate space 300 with respect to the registration element 170.

In some instances, the system 100 may further include a computerized tomography device 700 (see, e.g., FIG. 5) arranged to conduct a radiographic scan of the housing 240, and the object 200 and support element 220 housed therein, to form a radiographic image thereof (see, e.g., FIG. 6, left side image), prior to the registration element 170 being engaged with the object 200 or the support element 220. In such instances, the controller 190 is arranged to be in communication with the computerized tomography device 700 to receive the imaging data, representing the radiographic scan/radiographic image, therefrom. Upon receipt of the imaging data, the controller 190 is further arranged to image-match the radiographic image of the object 200 with the three-dimensional surface image of the object 200 (see, e.g., FIG. 6) so as to form a correlated image of the object 200 in relation to the registration element 170. Once the radiographic image and the three-dimensional surface image are correlated, the controller 190 is arranged to correlate the object 200 with the registration element 170 in the correlated image so as to register the object 200 with the coordinate system 300.

The controller 190 is arranged to allow formation of a plan of a procedure on the object 200 in relation to the three-dimensional surface image thereof prior to the object 200 being correlated with the registration element 170 in the three-dimensional surface image thereof. If the optical scanner 400 is engaged with the robot tracking arm 500, the controller 190 may be further arranged to track a position of the robot tracking arm 500 and the optical scanner 400 operably engaged with the distal end 520 thereof in relation to the coordinate system 300. In either instance, once the object 200 is correlated with the registration element 170, as determined with respect to the coordinate system 300 associated with the registration element 170 in the three-dimensional surface image from the optical surface scan, the plan of the procedure, which was determined and developed with respect to the three-dimensional surface scan, can be subsequently used to guide a robot 800, such as a surgical robot, having a surgical instrument 820 engaged therewith (and operably engaged with the robot tracking arm 500 in communication with the registration element 170 affixed to the patient) to execute the plan of the procedure by the surgical instrument 820 on the object 200 in relation to the registration of the object 200 with the coordinate system 300.

In one aspect of the present disclosure, a method of relating an object 200 to a coordinate system 300 involves an arrangement wherein the object 200 is supported by a support element 220, and wherein the object 200 and the support element 220 are housed within a housing 240. In one example, such an arrangement may include a tooth as the object, the corresponding jaw and/or gums as the support element, and the mouth or maxillofacial structure as the housing. The method may thus include engaging a registration element 170 with the object or the support element (FIG. 7, block 900). In some instances, the registration element 170 is disposed in or otherwise exists in a known relation in or with the coordinate system 300, as disclosed herein. An optical surface scan of the object and the registration element, within the housing, is then conducted, using an optical scanner 400 (in some instances, the optical scanner 400 may be hand held and manually manipulated, or the optical scanner 400 may be operably engaged with a distal end 520 of a robot tracking arm 500), to form a three-dimensional surface image of the object in relation to the registration element 170 (FIG. 7, block 920). The optical surface scan by the optical scanner 400 digitizes the image of the object and the registration element 170, in the form of the three-dimensional surface image, and the three-dimensional surface image of the object is then correlated with the registration element, such that the object is then registered with the coordinate system (e.g., translate the image from an Image Coordinate Space (coordinate space internal to the image) to a Patient Coordinate Space (coordinate space in relation to the patient or the registration element 170)) (FIG. 7, block 940).

Another aspect of the present disclosure is directed to a method of controlling a robot 800 with respect to an object 200 in a coordinate system 300, wherein such a method involves an arrangement having the object 200 supported by a support element 220, and with both the object 200 and the support element 220 being housed within a housing 240. In one example, such an arrangement may include a tooth as the object, the corresponding jaw and/or gums as the support element, and the mouth or maxillofacial structure as the housing. The method may thus include engaging a registration element 170 with the object 200 or the support element 220 (FIG. 8, block 1000) and then conducting an optical surface scan of the object and the registration element, using an optical scanner 400 (in some instances, the optical scanner 400 may be hand held and manually manipulated, or the optical scanner 400 may be operably engaged with a distal end 520 of a robot tracking arm 500), to form a three-dimensional surface image of the object, wherein the three-dimensional surface image has the coordinate system 300 associated therewith, and wherein the registration element 170 is associated with the coordinate system 300 (FIG. 8, block 1020). A plan of a procedure on the object is formed (FIG. 8, block 1040), for example, from the three-dimensional surface image, prior to correlating the object with the registration element in the three-dimensional surface image so as to register the object with the coordinate system (e.g., translate the image from an Image Coordinate Space (coordinate space internal to the image) to a Patient Coordinate Space (coordinate space in relation to the patient or the registration element 170)) (FIG. 8, block 1060). A robot 800 having a surgical instrument 820 engaged therewith may then be guided to execute the plan of the procedure by the surgical instrument 820 on the object 200 in relation to the registration of the object 200 with the coordinate system 300 (FIG. 8, block 1080).

In some aspects, particularly in relation to the two method aspects disclosed hereinabove, a radiographic scan of the housing, and the object and support element housed therein, may be conducted to form a radiographic image of the housing, object, and support element, prior to the registration element being engaged with the object or the support element (FIG. 7, block 960, FIG. 8, block 1100). The radiographic image of the object is then image-matched with the three-dimensional surface image of the object so as to form a correlated image of the object in relation to the registration element (FIG. 7, block 970, FIG. 8, block 1120). The object is then correlated with the registration element in the correlated image so as to register the object with the coordinate system (e.g., translate the correlated image from an Image Coordinate Space (coordinate space internal to the correlated image) to a Patient Coordinate Space (coordinate space in relation to the patient or the registration element 170)) (FIG. 7, block 980, FIG. 8, block 1140).

In some aspects, image-matching the radiographic image with the three-dimensional surface image may involve image-matching a three-dimensional structural representation of the object and the support element provided by the radiographic scan with the three-dimensional surface image of the object, the support element, and the registration element provided by the optical surface scan. In this manner, the plan for the procedure may then be formed based on and in consideration of both the aesthetic aspects of the procedure seen in the three-dimensional surface image of the optical surface scan (e.g., an intra-oral scan showing, for example, the gum and soft tissue about the tooth) as well as particular anatomic structures of interest seen in the three-dimensional structural representation of the radiographic scan (e.g., a computerized tomography (CT) scan showing, for example, the nerves, teeth roots, jawbones, and/or relate structure).

In some instances, since the registration element is associated with the optical surface scan, the registration element need not be radiopaque, but may be radiopaque if necessary or desired. In other instances, the registration element 170 may include, e.g., one or more fiducial markers, fiducial beads, etc., engaged with a reference frame (e.g., a splint), prior to the reference frame being engaged with the object or the support element. Engagement with the object (e.g., tooth) or the support element (e.g., gums or jaw) with the reference frame (e.g., splint) may be accomplished, for example, by way of a suitable adhesive (e.g., an epoxy) disposed therebetween. In other instances, for example, in the case of an edentulous patient, an implant anchor may be implanted in a jawbone and the reference frame (e.g., splint) may be securely attached thereto by a removable fastener.

In still other instances, the registration element may be arranged/configured to be in a known relation with the coordinate system. For example, the optical surface scanning device (e.g., the intra-oral scanning device, intra-oral scanner, or any other suitable light- or optical-based three-dimensional surface scanner/digitizer) may be operably engaged with the distal end of a robot tracking arm. The robot tracking arm, in turn, may be tracked by a controller in communication therewith, and the known or tracked position of the robot tracking arm may include the distal end thereof. Since the intra-oral scanner is engaged with the distal end of the robot tracking arm in such instances, the position of the imaging portion of the intra-oral scanner may also be known by the controller. The known position(s) of the robot tracking arm, as well as the intra-oral scanner engaged with the distal end of the robot tracking arm allows the controller to associate a coordinate system with the position(s) of the robot tracking arm and the intra-oral scanner. Further, the intra-oral scanner may be configured and arranged such that the digitized image of the registration element (and/or e.g., one or more fiducial markers engaged therewith) includes or is indicative of a ranging relationship (e.g., distance between the imager of the intra-oral scanner and a point on the imaged surface) between the intra-oral scanner and the imaged object. With such a ranging relationship, the relation of the registration element with the coordinate system is known to the controller upon being imaged by the intra-oral scanner engaged with the distal end of the robot tracking arm.

In other instances, the relation of the registration element with the coordinate system may be known or determinable in different manners in addition to or in the alternative to the relation between the intra-oral scanner and the registration element. For example, an emitter-detector arrangement may be provided in communication between the registration element and the intra-oral scanner and/or the robot tracking arm. In other instances, a transceiver-transceiver arrangement, a transceiver-reflector arrangement, a transmitter-receiver arrangement, or a sensor arrangement, as appropriate, may be implemented such that the registration element is in communication with and in a known position with respect to the intra-oral scanner/robot tracking arm, and therefore disposed in a known relation with respect to the coordinate system.

Once the optical surface scan is completed, the procedure on the object can then be planned in relation to the three-dimensional surface image of the object either before or after the object is correlated with the registration element in the three-dimensional surface image thereof. In some particular aspects, the procedure on the object is planned in relation to the three-dimensional surface image of the object prior to the object being correlated with the registration element in the three-dimensional surface image thereof so as to register the object and the planned procedure with the coordinate system. In instances of a robotic surgical procedure being planned, a robot (or a robot arm supporting a surgical tool for carrying out the surgical procedure) can then be guided by the controller to execute the plan of the procedure on the object using the surgical tool in relation to the registration of the object with the coordinate system. Such procedure planning and robot guidance based on the optical surface scan may be advantageous, for example, in instances where the planned procedure is on the object itself (e.g., a tooth), or otherwise involves a surface feature related to or associated with the object. In one instance, such a procedure may involve abrading the object (tooth) in preparation for receiving a crown.

In instances where a radiographic scan (e.g., a computerized tomography (CT) scan) is also conducted prior to the optical surface scan, the radiographic image may be correlated with the three-dimensional surface image, for example, using an image-matching procedure implemented by the controller or other suitable computer device in receipt of the data for both the radiographic scan and the optical surface scan. That is, in some aspects, a three-dimensional structural representation of the object and the support element provided by the radiographic scan may be image-matched (e.g., based on anatomical features common to both images) with the three-dimensional surface image of the object, the support element, and the registration element provided by the optical surface scan to form a correlated image. Once the correlated image is formed, the object can then be correlated with the registration element in the correlated image so as to register the object with the coordinate system. Depending on the nature of the procedure (e.g., whether the procedure is to be conducted on anatomical features/structure underlying the surface, on surface features, or both), the procedure on the object may be planned in relation to the three-dimensional surface image thereof from the optical surface scan, from the radiographic image thereof from the radiographic scan, or from the correlated image thereof including the three-dimensional surface image and the radiographic image. In this manner, the procedure on the object may also be planned prior to the object being correlated with the registration element in the correlated image thereof.

The disclosed methods and systems thus reduce or eliminate the need for a second radiographic scan (e.g., CT scan) as part of a pre-operative process for a robotic surgical procedure, and it may be advantageous to reduce the x-ray exposure of the patient by removing this second radiographic scan. By taking an optical three-dimensional surface scan of the feature of interest (e.g., an intra-oral scan) and including the fiducial marker array (e.g., mounted on the splint, with the splint engaged with the patient) in the intra-oral scan, the imaged fiducial marker array in the scan is used to register the optical three-dimensional surface scan with the patient and/or the locations of the features (e.g., anatomical features). Once the optical three-dimensional surface scan is registered with the coordinate system associated with the fiducial marker array engaged with the patient, the imaged features (e.g., the three-dimension surface image of the anatomy) from the intra-oral scan can be can be registered with the imaged features (e.g., the radiographic image of the structure of the anatomy) from the original/first CT scan. The plan for the procedure and other information associated therewith, developed from the original/first CT scan, can then be applied in reference to the patient and/or the locations of the anatomical features of the patient (e.g., within the coordinate system associated with the fiducial marker array) based on the relation to the coordinate system provided by the intra-oral scan.

In further aspects, the optical three-dimensional surface scan (e.g., intra-oral scan) may eliminate the need for both the first and second CT scans. For example, in some cases, the surgeon may not need a CT scan (e.g., radiographic imaging of anatomical features) to accomplish the intended procedure. This could be applicable to robotic procedures beyond, for instance, dental implants, and extend to, for instance, a tooth preparation procedure involving drilling or abrading away a tooth surface (e.g., to eliminate decayed areas of the tooth) and prepare the remaining portion of the tooth for receiving a crown (e.g., a prosthetic tooth) thereon. In such instances, the intra-oral scan alone may be sufficient for the purpose of planning the procedure, and the fiducial marker array included in the intra-oral scan can be used to register the intra-oral scan with the patient and/or the locations of the features of the patient (e.g., within the coordinate system associated with the fiducial marker array).

The implementation of the optical surface scan using, for example, an intra-oral scanner, allows the mouth (or teeth therein) and the fiducial marker to be scanned and imaged during surgery while the patient is unconscious, whereas the patient must often be awake and conscious during a CT scan with the fiducial marker(s) in place. The image from the intra-oral scan (with the fiducial marker(s) in place) can then be correlated with the image from the prior CT scan (without the fiducial marker(s) in place) by matching the anatomical geometry or features between the images. Since the imaging captured by the intra-oral scanner is already related to the fiducial marker(s) and thus integrated into and registered with the Patient Coordinate Space via interaction with the fiducial marker(s), the intra-oral scan/image (and the CT scan/image, if implemented), including the object and the fiducial marker(s), is thus readily relatable to the mechanical tracking (robot) arm in registration with the Patient Coordinate Space reference and thus can be readily integrated into the robotic system overall to guide the robot in the procedure.

Many modifications and other aspects of the disclosure set forth herein will come to mind to one skilled in the art to which this disclosure pertain having the benefit of the teachings presented in the foregoing descriptions and the associated drawings. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for purposes of limitation.

It should be understood that although the terms first, second, etc. may be used herein to describe various steps or calculations, these steps or calculations should not be limited by these terms. These terms are only used to distinguish one operation or calculation from another. For example, a first calculation may be termed a second calculation, and, similarly, a second step may be termed a first step, without departing from the scope of this disclosure. As used herein, the term "and/or" and the "/" symbol includes any and all combinations of one or more of the associated listed items.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

That which is claimed:

1. A method of relating an object to a coordinate system, the object being supported by a support element, the object and the support element being housed within a housing, the method comprising:
   engaging a registration element, comprising one or more fiducial markers, with the object or the support element;
   conducting an optical surface scan of the object and the registration element, using an optical scanner, to form a three-dimensional surface image of the object, the three-dimensional surface image having the coordinate system associated therewith, such that the registration element is associated with the coordinate system;
   determining a distance between the registration element and the optical scanner according to a ranging relationship between the optical scanner and the object to determine a relation between the registration element and the coordinate system;
   correlating the object with the registration element in the three-dimensional surface image, using a controller having a processor and being in communication with the optical scanner, to determine a relationship between the object and the registration element, the object thereby being registered with the coordinate system via the determined relationship with the registration element; and
   planning a procedure, the procedure being a robotic procedure to be conducted by a robot on the object, using the controller, in relation to the three-dimensional surface image thereof prior to correlating the object with the registration element in the three-dimensional surface image.

2. The method of claim 1, comprising:
   conducting a radiographic scan of the housing, and the object and support element housed therein, to form a radiographic image, prior to engaging the registration element with the object or the support element;
   image-matching the radiographic image of the object with the three-dimensional surface image of the object so as to form a correlated image of the object in relation to the registration element; and
   correlating the object with the registration element in the correlated image according to the relationship between the object and the registration element, such that the object is registered with the coordinate system via the determined relationship with the registration element.

3. The method of claim 2, wherein image-matching the radiographic image with the three-dimensional surface image comprises image-matching a three-dimensional structural representation of the object and the support element provided by the radiographic scan with the three-dimensional surface image of the object, the support element, and the registration element provided by the optical surface scan.

4. The method of claim 1, comprising operably engaging the optical scanner with a distal end of a robot tracking arm registered with the coordinate system.

5. The method of claim 1, wherein engaging the registration element with the object or the support element comprises:
   engaging the registration element with a reference frame; and
   engaging the reference frame with the object or the support element.

6. A system for relating an object to a coordinate system, the object being supported by a support element, the object and the support element being housed within a housing, the system comprising:
   a registration element, comprising one or more fiducial markers, adapted to be engaged with the object or the support element;
   an optical scanner arranged to conduct an optical surface scan of the object and the registration element and to form a three-dimensional surface image of the object, the three-dimensional surface image having the coordinate system associated therewith, such that the registration element is associated with the coordinate system; and
   a controller having a processor and being in communication with the optical scanner, the controller being arranged to determine a distance between the registration element and the optical scanner according to a ranging relationship between the optical scanner and the object to determine a relation between the registration element and the coordinate system, and to correlate the object with the registration element in the three-dimensional surface image to determine a relationship between the object and the registration element, the object thereby being registered with the coordinate system via the determined relationship with the registration element, and to allow formation of a plan of a procedure, the procedure being a robotic procedure to be conducted by a robot on the object in relation to the three-dimensional surface image thereof prior to correlating the object with the registration element in the three-dimensional surface image.

7. The system of claim 6, comprising a computerized tomography device arranged to conduct a radiographic scan of the housing, and the object and support element housed therein, to form a radiographic image, prior to the registration element being engaged with the object or the support element, wherein the controller is arranged to be in communication with the computerized tomography device, to image-match the radiographic image of the object with the three-dimensional surface image of the object so as to form a correlated image of the object in relation to the registration element, and to correlate the object with the registration element in the correlated image according to the relationship between the object and the registration element, such that the object is registered with the coordinate system via the determined relationship with the registration element.

8. The system of claim 7, wherein the controller is arranged to image-match a three-dimensional structural representation of the object and the support element provided by the radiographic scan with the three-dimensional surface image of the object, the support element, and the registration element provided by the optical surface scan.

9. The system of claim 7, wherein the controller is arranged to allow formation of the plan of the robotic procedure on the object in relation to the radiographic image thereof, or the correlated image thereof including the three-dimensional surface image and the radiographic image.

10. The system of claim 6, wherein the optical scanner is operably engaged with a distal end of a robot tracking arm registered with the coordinate system and arranged to be in communication with the controller.

11. The system of claim 10, wherein the controller is arranged to track a position of the robot tracking arm and the optical scanner operably engaged with the distal end thereof in relation to the coordinate system.

12. The system of claim 10, wherein the optical scanner is arranged to be in communication with the robot.

13. The system of claim 6, comprising a reference frame having the registration element engaged therewith, the reference frame being engaged with the object or the support element.

14. The system of claim 6, wherein the controller is arranged in communication with a robot, and wherein the system is further arranged to guide the robot to execute the plan of the robotic procedure on the object in relation to the registration of the object with the coordinate system.

15. A method of controlling a robot with respect to an object in a coordinate system, the object being supported by a support element, the object and the support element being housed within a housing, the method comprising:
engaging a registration element, comprising one or more fiducial markers, with the object or the support element;
conducting an optical surface scan of the object and the registration element, using an optical scanner, to form a three-dimensional surface image of the object, the three-dimensional surface image having the coordinate system associated therewith, such that the registration element is associated with the coordinate system;
determining a distance between the registration element and the optical scanner according to a ranging relationship between the optical scanner and the object to determine a relation between the registration element and the coordinate system;
planning a procedure, the procedure being a robotic procedure to be conducted by a robot on the object;
correlating the object with the registration element in the three-dimensional surface image using a controller having a processor and being in communication with the optical scanner, to determine a relationship between the object and the registration element, the object thereby being registered with the coordinate system via the determined relationship with the registration element; and
guiding a robot to execute the plan of the robotic procedure on the object in relation to the registration of the object with the coordinate system.

16. The method of claim 15, comprising:
conducting a radiographic scan of the housing, and the object and support element housed therein, to form a radiographic image, prior to engaging the registration element with the object or the support element;
image-matching the radiographic image of the object with the three-dimensional surface image of the object so as to form a correlated image of the object in relation to the registration element; and
correlating the object with the registration element in the correlated image according to the relationship between the object and the registration element, such that the object is registered with the coordinate system via the determined relationship with the registration element.

17. The method of claim 16, wherein image-matching the radiographic image with the three-dimensional surface image comprises image-matching a three-dimensional structural representation of the object and the support element provided by the radiographic scan with the three-dimensional surface image of the object, the support element, and the registration element provided by the optical surface scan.

18. The method of claim 16, wherein planning the robotic procedure on the object comprises planning the robotic procedure on the object, using the controller, in relation to the three-dimensional surface image thereof, the radiographic image thereof, or the correlated image thereof including the three-dimensional surface image and the radiographic image.

19. The method of claim 16, wherein planning the robotic procedure on the object comprises planning the robotic procedure on the object prior to correlating the object with the registration element in the correlated image.

20. The method of claim 15, comprising operably engaging the optical scanner with a distal end of a robot tracking arm registered with the coordinate system and arranged to be in communication with the robot.

21. The method of claim 15, wherein engaging the registration element with the object or the support element comprises:
engaging the registration element with a reference frame; and
engaging the reference frame with the object or the support element.

* * * * *